United States Patent
House (10) Patent No.: US 7,601,142 B2
(45) Date of Patent: Oct. 13, 2009

(54) DEVICES FOR CONNECTING CATHETER ASSEMBLY TO COLLECTION RECEPTACLE

(75) Inventor: Jamie Glen House, Colorado Springs, CO (US)

(73) Assignee: Colorado Catheter Company, Inc., Colorado Springs, CO (US)

( * ) Notice: Subject to any disclaimer, the term of this patent is extended or adjusted under 35 U.S.C. 154(b) by 232 days.

(21) Appl. No.: 11/546,293

(22) Filed: Oct. 12, 2006

(65) Prior Publication Data

US 2008/0171992 A1 Jul. 17, 2008

(51) Int. Cl.
*A61M 1/00* (2006.01)
*A61M 25/16* (2006.01)
*A61M 25/18* (2006.01)
*A61M 39/00* (2006.01)
*A61M 39/10* (2006.01)

(52) U.S. Cl. .......... 604/326; 604/533; 604/905
(58) Field of Classification Search ........ 604/905, 604/326, 533, 349–350, 180
See application file for complete search history.

(56) References Cited

U.S. PATENT DOCUMENTS

| | | | |
|---|---|---|---|
| 3,832,999 A * | 9/1974 | Crilly | ............ 604/185 |
| 4,622,033 A | 11/1986 | Taniguchi | |
| 4,752,292 A | 6/1988 | Lopez et al. | |
| 4,772,275 A | 9/1988 | Erlich | |
| 4,781,702 A | 11/1988 | Herrli | |
| 4,834,710 A | 5/1989 | Fleck | |
| 4,840,625 A | 6/1989 | Bell | |
| 5,149,326 A | 9/1992 | Woodgrift et al. | |
| 5,181,913 A | 1/1993 | Erlich | |
| 5,607,406 A | 3/1997 | Hernandez et al. | |
| 5,779,670 A | 7/1998 | Bidwell et al. | |
| 5,792,114 A | 8/1998 | Fiore | |
| 5,848,997 A * | 12/1998 | Erskine et al. | ............ 604/533 |
| 5,895,374 A | 4/1999 | Rodsten | |
| 6,053,905 A | 4/2000 | Daignault et al. | |
| 6,059,107 A | 5/2000 | Nosted et al. | |
| 6,090,075 A | 7/2000 | House | |
| 6,176,849 B1 | 1/2001 | Yang et al. | |
| 6,217,569 B1 | 4/2001 | Fiore | |
| 6,409,717 B1 | 6/2002 | Israelsson et al. | |
| 6,471,684 B2 | 10/2002 | Dulak et al. | |
| 6,578,709 B1 | 6/2003 | Kavanagh et al. | |
| 6,602,244 B2 | 8/2003 | Kavanagh et al. | |
| 6,634,498 B2 | 10/2003 | Kayerod et al. | |
| 6,673,053 B2 | 1/2004 | Wang et al. | |
| 6,736,805 B2 | 5/2004 | Israelsson et al. | |
| 6,848,574 B1 | 2/2005 | Israelsson et al. | |
| 7,390,028 B2 * | 6/2008 | Blazek | ............ 285/317 |
| 2001/0001443 A1 | 5/2001 | Kayerod et al. | |
| 2001/0007060 A1 | 7/2001 | Fiore | |
| 2001/0027295 A1 | 10/2001 | Dulak et al. | |
| 2001/0027299 A1 | 10/2001 | Yang et al. | |
| 2003/0018302 A1 | 1/2003 | Kavanagh et al. | |

(Continued)

FOREIGN PATENT DOCUMENTS

GB  2219507 A  * 12/1989

*Primary Examiner*—Nicholas D Lucchesi
*Assistant Examiner*—Rebecca E Eisenberg
(74) *Attorney, Agent, or Firm*—Moazzam & Associates, LLC (57) ABSTRACT

A device for connecting a catheter assembly to a collection receptacle is disclosed. The device is situated at a distal portion of the catheter assembly and the connection made may be either temporary or permanent.

4 Claims, 4 Drawing Sheets

U.S. PATENT DOCUMENTS

| | | |
|---|---|---|
| 2004/0024381 A1* | 2/2004 | Kurth et al. .................. 604/533 |
| 2004/0074794 A1 | 4/2004 | Conway et al. |
| 2004/0153051 A1 | 8/2004 | Israelsson et al. |
| 2004/0256264 A1 | 12/2004 | Israelsson et al. |
| 2005/0015076 A1 | 1/2005 | Giebmeyer et al. |
| 2005/0033268 A1* | 2/2005 | Decaria ...................... 604/533 |
| 2005/0109648 A1 | 5/2005 | Kerzman et al. |
| 2005/0137582 A1 | 6/2005 | Kull-Osterlin et al. |
| 2006/0025753 A1 | 2/2006 | Kubalak et al. |
| 2006/0122568 A1 | 6/2006 | Elson et al. |
| 2007/0066965 A1* | 3/2007 | Coambs et al. ............. 604/533 |

* cited by examiner

DEVICES FOR CONNECTING CATHETER ASSEMBLY TO COLLECTION RECEPTACLE

BACKGROUND OF THE INVENTION

1. Field of the Invention

The present invention relates to catheter assemblies. More particularly, the present invention relates to devices for connecting a distal portion of a catheter assembly to a collection receptacle.

2. Background of the Invention

The urinary catheterization procedure is a common medical practice with the procedure being performed today in both hospital and home settings. In hospital settings today, nurses often perform urinary catheterization procedures using convenience packs, or pre-assembled kits. These convenience packs typically contain a vinyl, red latex rubber, or silicon catheter, a waterproof absorbent underpad, a fenestrated drape, disposable gloves, a sealed packet containing about 22.5 mL of Povidone-Iodine solution, several prepping cotton balls in a disposable tray compartment, a sealed packet containing sterile lubricating jelly, a plastic forceps, a sterile specimen bottle, and a 1000 mL graduated basin. All of these items are packaged together and sterilized.

To perform the catheterization procedure, a nurse opens the tray, dons sterile gloves and places the drape around the patient's genitalia. The Povidone-Iodine packet is opened and poured over the cotton balls. The packet of lubricating jelly is then opened and squeezed onto a sterile field. The patient's urethral opening is cleansed with the saturated cotton balls, holding each cotton ball with the forceps. Then, the nurse runs the tip end of the catheter, comprising the first inch or two (about 2.5 cm to about 5 cm) of the insertable portion, through the lubricating jelly. The catheter is then inserted into the patient's urethra and advanced until urine begins to flow through the catheter. The urine is drained into the 1000 mL graduated basin and a urine specimen is caught in the specimen bottle if needed. The catheter is then removed and all the aforementioned items are discarded. Care must be taken to maintain sterile procedure in order to reduce the risk of urinary tract infection.

In order to collect the drained fluid, the 1000 mL graduated basin is typically positioned between the patient's legs during catheterization. Therefore, the basin is susceptible to being struck by a spastic or an uncooperative patient. This can result in spilling of the collected fluid or in making it very difficult for the nurse to perform the catheterization. After the urine is collected, the nurse typically will carry the 1000 mL graduated basin to the toilet and pour out its contents. During this trip, the nurse may spill some of the urine due to difficulty in handling the filled basin or as a result of the nurse's stumbling during her walk from the patient's bed to the bathroom.

Because multiple steps are involved in the catheterization procedure (e.g., carrying the unwieldy urine filled 1000 mL graduated basin to the toilet) and meticulous attention to maintain sterile technique is required, a nurse typically spends a significant amount of time (e.g., 10-15 minutes) carrying out each catheterization. This basic procedure is used in virtually every inpatient hospital around the world, and has remained essentially the same for 50 years.

Thus, there is a need in the healthcare industry for a more convenient and streamlined technique for collecting and disposing the fluid collected from the catheterization process.

SUMMARY OF THE INVENTION

The current techniques for catheterization are inefficient and inconvenient. In conventional catheterization techniques, the drained fluid is collected in a separate 1000 mL graduated basin which is positioned between the patient's legs. The 1000 mL graduated basin may cause problems for the nurse especially when the patient is spastic or uncooperative since the patient can strike and shift the basin. Also, the basin is unwieldy after it is filled thus making it difficult to carry to the bathroom to empty. The present invention addresses this healthcare problem by providing various techniques for connecting a catheter assembly to a collection receptacle. More specifically, the present invention proposes a device on a distal portion of a catheter assembly in order to facilitate the collection and emptying of the drained fluid.

In one exemplary embodiment, the present invention is a connecting device for a catheter assembly. The device includes a body situated at a distal portion of a catheter assembly; and a collar, wherein the body mates with the collar thereby allowing fluid communication within the catheter assembly while maintaining a temporary or permanent seal preventing fluid communication with an external environment.

In another exemplary embodiment, the present invention is a connecting device for a catheter assembly. The device includes a circular body situated at a distal portion of a catheter assembly on or proximal to a urine outlet piece; and a collar situated at a proximal portion of a collection receptacle, wherein the circular body mates with the collar thereby allowing fluid communication between the urine outlet piece and the collection receptacle while maintaining a temporary or permanent seal preventing fluid communication with an external environment.

In yet another exemplary embodiment, the present invention is a catheter assembly. The assembly includes an apertured body situated at a distal portion of the assembly grippable by the operator's hand; a receiving collar situated at a proximal portion of a collection receptacle grippable by the operator's other hand; and a catheter passing through the aperture of the apertured body in fluid communication with the receiving collar.

DETAILED DESCRIPTION OF THE INVENTION

The present invention provides for catheter and catheter assemblies with connection devices such that the catheter and catheter assemblies are readily attached to and detached from collection receptacles. In particular embodiments and examples presented herein, such catheters are described with respect to urinary catheterization but it must be noted that such connection devices according to the present invention are not limited to urinary catheters alone but may be applicable to any catheter and catheter assembly that could benefit from the use of such connection devices. Furthermore, the present invention allows for an efficient connection of a collection bag and an easier technique for collecting the drained fluid so as to decrease the time required for catheterization and increase the reliability and sterility of catheterization and associated procedures.

Figure 1A:
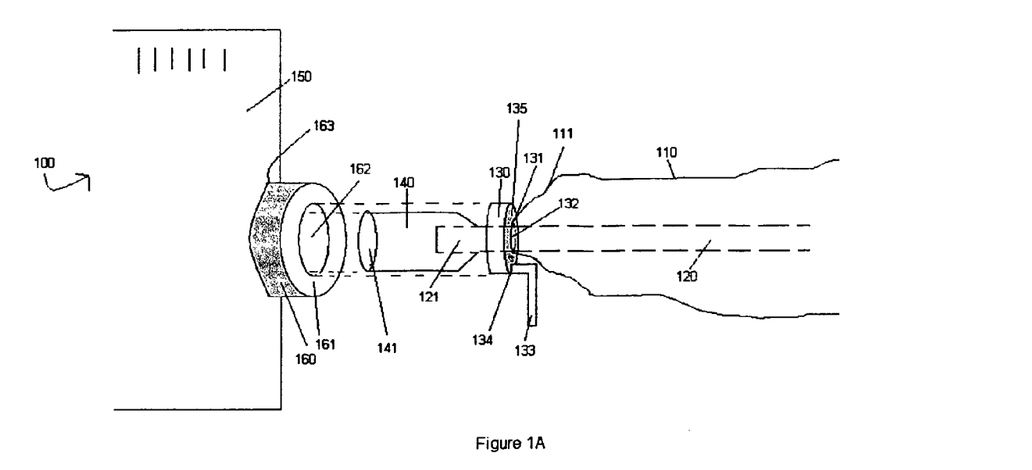
FIG. 1A shows a side view of a catheter assembly with a mating stopper with an optional grippable arm at a distal portion of the catheter assembly according to an exemplary embodiment of the present invention.

An exemplary embodiment of the present invention as used in catheter assembly 100 is shown in FIG. 1A. Assembly 100 includes a mating stopper 130 situated at the distal end of the catheter assembly, a catheter 120, a protective sheath 110, a distal end 140, a urine outlet 141, a collection receptacle 150, and a mating collar 160. The mating stopper 130 may be composed of a conventional material commonly used in the catheter arts or more specifically, a rubber or plastic material, so that a substantially tight seal is maintained between the mating stopper 130 and the mating collar 160. The mating stopper 130 may be bound via any adhesive technique commonly used in the catheter arts so that it is stationary and unable to translate the length of the assembly 100. The mating stopper 130 may be of a diameter slightly smaller than of the diameter of the receiving aperture 162 such that the receiving aperture 162 receives and mates with the mating stopper 130 establishing a tight, leak free seal. The diameter of the distal end 140 may be smaller than the diameter of the receiving aperture 162 such that during connection, the distal end 140 resides within the collection receptacle 150 under the mating collar 160. Optionally, the mating stopper 130 and mating collar 160 may have a magnetic relationship with each other to either enhance the tight seal connection described above, or be a replacement for such a seal. Furthermore, all embodiments described herein may have a magnetic relationship between the mating ends of the distal end of the catheter assembly and the collar of the receptacle to enhance the reversible seal between the two ends.

The catheter 120 may be composed of a standard material commonly used in the catheter arts or it may be comprised of a hydrophilic material in order to further lubricate the catheter 120. The protective sheath 110 may be attached to the catheter assembly at attachment site 131 at the distal terminus 111 of the protective sheath 110. The protective sheath 110 can be attached at attachment site 131 by various adhesive methods known to one having ordinary skill in the catheter art as long as a contamination free seal is maintained. The protective sheath 110 may serve to maintain catheter sterility and provide a chamber for additional lubricant or aqueous solution for the catheter 120. The attachment site 131 can be situated as shown in FIG. 1A bound to the stopper surface 135 or it can be situated just proximal to the stopper surface 135 or just distal to the stopper surface 135 on the under-side of the mating stopper 130.

The proximal tip 121 of catheter 120 may be positioned within the stopper aperture 132 and may extend into the distal end 140 of the catheter assembly. The stopper aperture 132 may be of a diameter slightly larger than the diameter of catheter 120 so that the catheter 120 is able to be positioned as shown in FIG. 1A. The catheter 120 may be surrounded and enveloped by the mating stopper 130 which keeps the catheter 120 stable and stationary.

During connection of the catheter assembly 100 to the collection receptacle 150, the operator may grasp the protective sheath 110 at the distal terminus 111 just proximal to the mating stopper 130 such that the operator's hand or thumb may be butted up against the stopper surface 135 in order to guide the mating stopper 130 into the mating collar 160 of the collection receptacle 150. With the other hand, the operator may grasp the collection receptacle 150 at the mating collar 160 or at the mating collar attachment site 163. The operator may guide the distal end 140 and mating stopper 130 towards the receiving aperture 162 of the mating collar 160. After the distal end 140 passes through the receiving aperture 162 and into the collection receptacle 150, the operator continues to guide the mating stopper 130 into the receiving aperture 162 until the mating stopper 130 is tightly mated with the mating collar 160 providing a tight, leak free seal. To make this seal, the operator guides the mating stopper 130 into the receiving aperture 162 so that the stopper surface 135 is at least flush with (e.g., occupying the same horizontal plane) mating collar surface 161.

The operator may continue to further guide the mating stopper 130 into the mating collar 160 if so desired but the operator may experience a stoppage point at which an optional grippable arm 133 prevents further guidance by acting as a backstop to further penetration into the receiving aperture 162. This optional grippable arm 133 thus may serve to prevent the mating stopper 130 from penetrating too far into the receiving aperture 162 making it difficult to detach the mating stopper 130 from the mating collar 160. Additionally, the optional grippable arm 133 may also serve as a grippable extension which can be used to further manipulate the catheter assembly 100 during attachment and detachment. The optional grippable arm 133 may be connected to the mating stopper 130 via attachment site 134 as shown in FIG. 1A. The optional grippable arm 133 may be L-shaped as depicted in FIG. 1A or it may assume any other shape such that it serves the functions as described above.

After the connection is made between the mating stopper 130 and the mating collar 160, the drained fluid may flow through the catheter 120 into the distal end 140 out through the urine outlet 141. The flow of the fluid may be contained and directed into the collection bag 150 since the distal end 140 is cylindrically shaped and the urine outlet 141 is situated within the collection bag 150 and past the mating collar 160. After the fluid is collected in the collection receptacle 150, the operator may grasp the optional grippable arm 133 and separate the mating stopper 130 from the mating collar 160 so as to expose the distal end 140 and urine outlet 141 to the external environment.

Figure 1B:
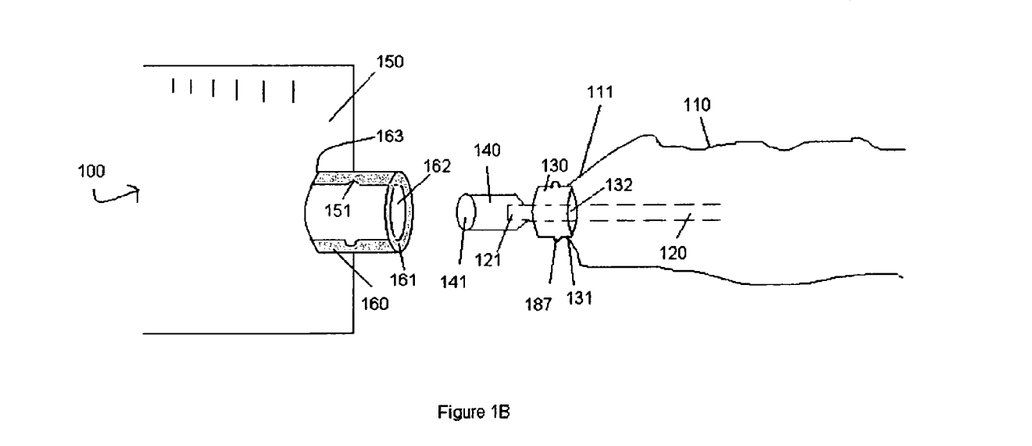
FIG. 1B shows a side view of a catheter assembly with a mating stopper with snap protrusions at a distal portion of the catheter assembly according to an exemplary embodiment of the present invention.

Another exemplary embodiment of the present invention incorporated into a catheter assembly 100 is shown in FIG. 1B. Assembly 100 in FIG. 1B includes labeled components possessing similar characteristics and parameters as the corresponding labeled components in FIG. 1A. However, the assembly in FIG. 1B includes snap wells 151 on the inside surface of mating collar 160, and snap protrusions 187 on the outer surface of mating stopper 130. These alternative structures may provide a tighter connection between the mating stopper 130 and the mating collar 160 so as to avoid undesired detachment or translation of the mating stopper 130. The exemplary embodiment shown in FIG. 1B may utilize both a physical mating technique (e.g., between the snap protrusions 187 and the snap wells 251) along with a frictional force technique (e.g., the force observed between the outer surface of mating stopper 130 and the inner surface of mating collar 160 during connection and disconnection) in order to provide a tighter and more secure distal end connection for assembly 100.

During connection, the user may grasp the distal terminus 111 of sheath 110 just proximal to attachment site 131 so that the user's hand is adjacent to or on the surface of the mating stopper 130. With the other hand, the user may grasp the mating collar 160 near mating collar attachment site 163 in such a way as to avoid blocking the receiving aperture 162 while maintaining a stable and secure grip on the mating collar 160. Then, the user may guide the mating stopper 130 with snap protrusions 187 into the receiving aperture 162 far enough so that the snap protrusions 187 reach the snap wells 151 and mate with them. As the mating stopper 130 is guided into the receiving aperture 162 and into the mating collar 160, the user may experience a frictional force opposed to the direction of force being applied by the user. This frictional force may be so strong as to provide a stable and guided introduction of the mating stopper 130 until the snap protrusions 187 reach and mate with the snap wells 151, but the frictional force may not be so strong so as it to make it difficult and/or unduly burdensome to insert the mating collar 130 into the mating collar 160. Also, the same frictional force may be observed in the opposite direction during disconnection and may serve to prevent premature disconnection, but it may not be so strong so as to make it difficult and/or unduly burdensome to detach the mating stopper 130 from the mating collar 160. Thus, during disconnection, the user my exert enough force (e.g., by pulling the mating stopper 130 apart from the mating collar 160) so as to overcome the opposing frictional force which may be serving to secure the mating stopper 130 to the mating collar 160.

In light of the parameters given above regarding the frictional force between the mating stopper 130 and the mating collar 160, the mating stopper 130 may be of a slightly smaller diameter than the mating collar 160 so as to allow the mating stopper 130 to slide into the mating collar 160 until the snap protrusions 187 reach and mate with the snap wells 151. The snap protrusions 187 may extend off of the surface of the mating stopper 130 as shown in FIG. 1B. The mating stopper 130 and the mating collar 160 may be composed of any commonly used flexible material in the catheter arts such that it may function as specified above which may include but is not limited to red rubber or silicon.

Figure 2:
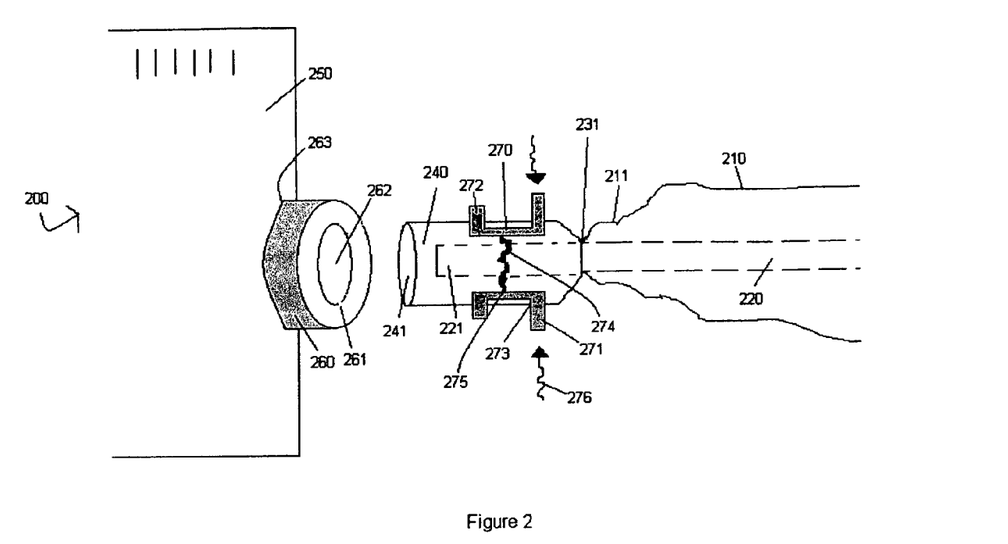
FIG. 2 shows a side view of a catheter assembly with mating releases separated by a spring at a distal portion of the catheter assembly according to an exemplary embodiment of the present invention.

Another exemplary embodiment of the present invention incorporated into a catheter assembly 200 is shown in FIG. 2, and includes mating releases 270 situated at the distal end of the catheter assembly, a spring 274, a catheter 220, a protective sheath 210, a distal end 240, a urine outlet 241, a collection receptacle 250, and a mating collar 260. The mating releases 270 may be composed of a standard material commonly used in the catheter arts. The mating releases 270 may be C-shaped as depicted in FIG. 2 or they may be of any design provided that they abide by the limitations and serve the functions as described below.

The mating releases 270 have shorter ends 272 and longer ends 271. The mating releases 270 are connected to each other by a spring 274. The spring is attached to the mating releases 270 at spring attachments 275. The spring 274 allows the operator to manipulate the mating releases 270 from a resting state in which the shorter ends 272 project off of the distal end 240 to an engaged state in which the shorter ends 272 are flush with the surface of the distal end 240. The spring 274 may be of such elastic strength that the mating releases 270 appear as depicted in FIG. 2 in the resting form while at the same time the mating releases 270 experience an amount of resistance such that the operator does not have any difficulty in manipulating the mating releases 270 into their engaged form. During the operator's manipulation of the mating releases 270 for connecting the distal end 240 to the mating collar 260, the longer ends 271 are grasped and pushed inside the distal end 240 as depicted in FIG. 2 in the direction of the arrows 276 such that the mating releases 270 approach the proximal tip 221. The longer ends 271 are pushed into the distal end 240 far enough such that the shorter ends 272 are flush with the surface of the distal end 240. The shorter ends 272 are shorter than the longer ends 271 since the shorter ends 272 only have to be long enough to catch and mate with the underside of the mating collar 260 in the resting state thus providing a technique for binding the distal end 240 with a collection receptacle 250. The longer ends 271 may be longer than the shorter ends 272 in order to make it easier for the operator to grasp and manipulate the longer ends 271. After the operator lets go of the longer ends 271 of the mating releases 270 from an engaged state, the spring 274 may have enough resiliency such that the mating releases 270 resume their resting state as depicted in FIG. 2.

Although no exact measurements are required for this exemplary embodiment of the present invention, the following parameters may be met: (1) the distance between the 2 mating releases in their engaged form is greater then the diameter of the catheter 220; (2) the length of the shorter ends 272 is such that when the mating releases 270 are in a resting state the shorter ends 272 are long enough to extend past a mating collar attachment site 263; and (3) the length of the mating releases 270 between the shorter ends 272 and the longer ends 271 is at least equal to the height of a mating collar 260 such that when distal end 240 is connected to a mating collar 260 the shorter ends 272 are situated on the underside of a mating collar 260 inside the collection receptacle 250 and the longer ends 271 are situated on top of a mating collar surface 261.

During connection of catheter assembly 200 with a mating collar 260 the operator engages the long ends 271, guides the distal end 240 into the receiving aperture 262 until the shorter ends 272 are situated underneath a mating collar 260 and inside a collection receptacle 250, disengages the long ends 271 at which point the spring 274 transforms back into its resting state as shown in FIG. 2 and the shorter ends 272 mate with the underside of a mating collar 260. Thus, a connection is formed between distal end 240 and receiving collar 260. During disconnection of the catheter assembly 200 with a mating collar 260 the operator engages the long ends 271, guides the distal end 240 out of the receiving aperture 262 until the no part of urine outlet 241 is inside the receiving aperture 262, and then disengages the long ends 271.

The proximal tip 221 of catheter 220 may be situated distal to the shorter ends 272 as shown in FIG. 2 in order to avoid contamination of the drained fluid. The parameters for the other component pieces not mentioned for this exemplary embodiment are consistent with the corresponding component pieces disclosed above in the exemplary embodiment shown in FIG. 1 (e.g., the diameter of distal end 240 is smaller than the diameter of receiving aperture 262, attachment site 231 can be made by various adhesive methods known to one having ordinary skill in the catheter art as long as a contamination free seal is maintained, etc.).

Figure 3:
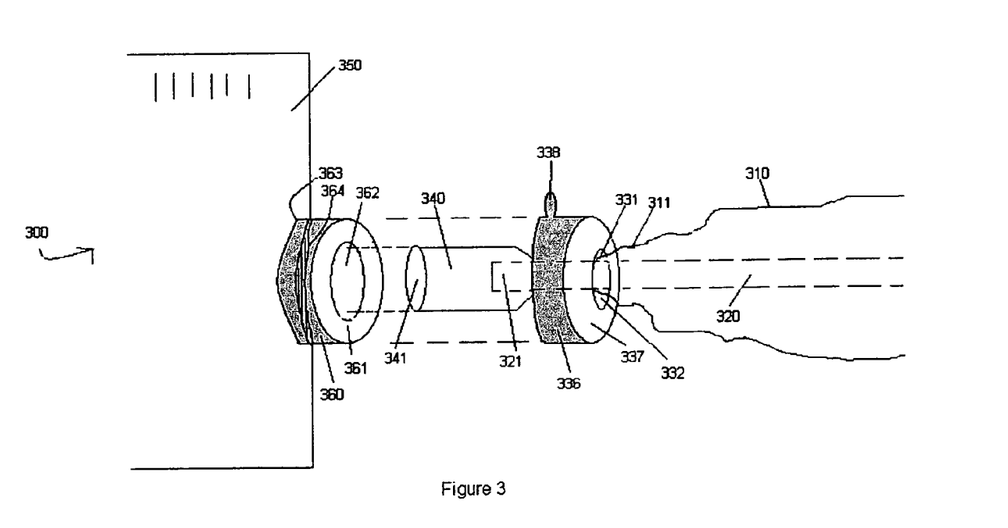
FIG. 3 shows a side view of a catheter assembly with a mating cap at a distal portion of the catheter assembly according to an exemplary embodiment of the present invention.

Another exemplary embodiment of the present invention incorporated into a catheter assembly 300 is shown in FIG. 3, and includes a mating cap 336 situated at the distal end of the catheter assembly, a catheter 320, a protective sheath 310, a distal end 340, a urine outlet 341, a collection receptacle 350, and mating collar 360 with a raised ring 364. The mating cap 336 may be bound to catheter assembly 300 by any adhesive method commonly used in the catheter arts. The mating cap 336 can be composed of any conventional material commonly used in the catheter arts as long as it can be pliable, and thus easily manipulated to mate with a raised ring 364 of the mating collar 360. The mating cap 336 may be of a diameter equal to or slightly larger than the diameter of the raised ring 364. In this way the mating cap 336 can be guided over the mating collar 360 far enough such that the mating cap 336 mates with the raised ring 364. Thus, during connection, the operator may grasp the cap surface 337 and snap the mating cap 336 over the raised ring 364. Since the mating cap 336 may be subjected to strong external forces (e.g., from the operator during connection), the mating cap 336 may be composed of a material capable of withstanding such forces and rebounding to form its original shape as depicted in FIG. 3. The raised ring 364 may be situated in the same horizontal plane as the mating collar attachment site 363 or just above it (e.g., towards the mating collar surface 361. An optional grasping tab 338 may be situated on the mating cap 336 in order to provide an extra surface for the operator to grip during connection and disconnection of the mating cap 336 and the mating collar 360.

During connection, the operator may grasp the cap surface 337, guide the distal end 340 into the receiving aperture 362 until the mating cap 336 makes contact with the raised ring 364. Upon contacting the raised ring 364, the operator snaps the mating cap 336 over the raised ring 364 such that a tight leak-free seal is made between the mating cap 336 and the mating collar 360. In the connected arrangement, the collar surface 361 makes contact with the underside of the cap surface 337 and the mating cap 336 occludes the portion of the mating collar 360 from just below the raised ring 364 to the collar surface 361. During disconnection, the operator may grasp the optional grasping tab 338 in order to open up space between the raised ring 364 and the mating cap 336. The operator then may pull the mating cap 336 back over the mating collar 360.

The mating cap 336 may be bound via any adhesive method commonly used in the catheter arts so that it is stationary and unable to translate the length of the assembly 300. The parameters for the other component pieces not mentioned for this exemplary embodiment are consistent with the corresponding component pieces disclosed above in the exemplary embodiment shown in FIG. 1 (e.g., the diameter of distal end 340 is smaller than the diameter of receiving aperture 362, attachment site 331 can be made by various adhesive methods known to one having ordinary skill in the catheter art as long as a contamination free seal is maintained, etc.).

Figure 4:
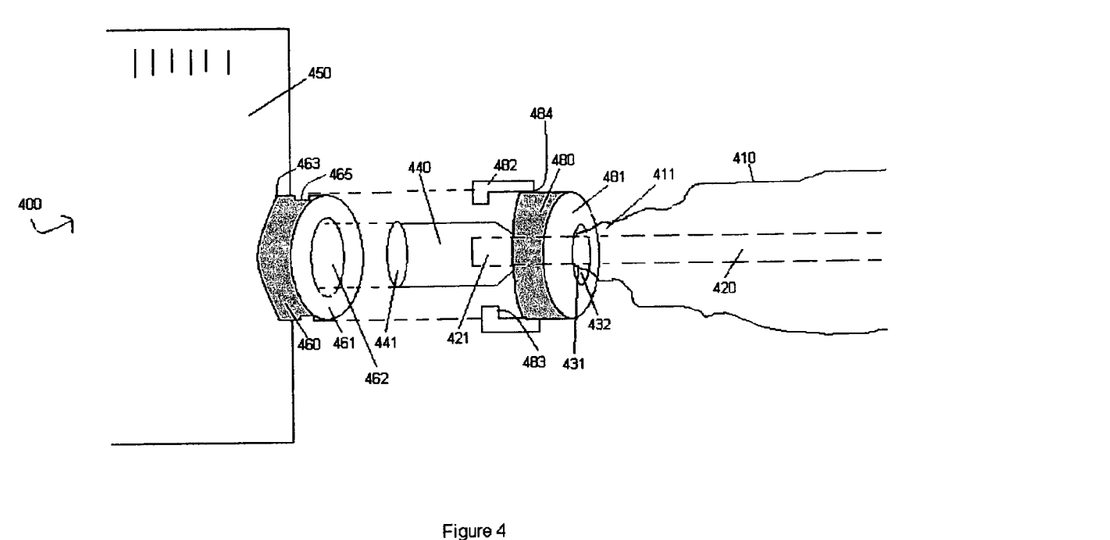
FIG. 4 shows a side view of a catheter assembly with mating connectors at a distal portion of the catheter assembly according to an exemplary embodiment of the present invention.

Another exemplary embodiment of the present invention incorporated into a catheter assembly 400 is shown in FIG. 4, and includes a mating piece 480 situated at the distal end of the catheter assembly with mating connectors 482, a catheter 420, a protective sheath 410, a distal end 440, a urine outlet 441, a collection receptacle 450, and a mating collar 460 with connection wells 465. The mating piece 480 has attached to its surface mating connectors 482 at attachment points 484. The mating connectors 482 can be composed of a conventional material commonly used in the catheter arts such that it can be pliable so the projections 483 of the mating connectors 482 can be pulled up and down without the mating connectors 482 breaking off of the mating piece 480. The mating connectors 482 can be attached to the mating piece 480 at attachment points 484 via various adhesive methods known to one having ordinary skill in the catheter arts as long as the adhesion can withstand ordinary pulling and pushing forces. The mating connectors 482 may be L-shaped as depicted in FIG. 4 or they may be of any other design provided that they serve the functions as described below. The mating piece 480 may be the same diameter as the mating collar 460. Both the mating piece 480 and the mating collar 460 can be composed of any standard material commonly used in the catheter arts. The mating piece 480 may be bound via any adhesive method commonly used in the catheter arts so that it is stationary and unable to translate the length of the assembly 400.

The connection wells 465 may be U-shaped indentations on the outside of the mating collar 460 as depicted in FIG. 4. The connection wells 465 can be made by any cutting techniques known to one having ordinary skill in the catheter arts. They may function to receive the projections 483 of the mating connectors 482 during connection. The connection wells 465 may be deep enough to accept and mate with the projections such that once mated, the projections 483 are locked into the connection wells 465 and any translational or rotational movement of catheter assembly 400 is prevented.

During connection, the mating piece 480 may be grasped at the mating piece surface 481, and the mating piece 480 may be guided towards the mating collar 460 such that the projections 483 slide over the mating collar 460 and mate with the connection wells 465 thus connecting the mating piece 480 with the mating collar 460. The length of the mating connectors 482 may be such that when connected with the connection wells 465, the underside of the mating piece 480 makes contact with and produces a tight, leak-free seal with the mating collar surface 461. During disconnection, the operator may grasp any portion of the mating connectors 482 and pull them out of the connection wells 465 such that the projections 483 break a horizontal plane covering the ridges of the connection wells 465 and the side portions of the mating collar 460. Once at least one mating connector 482 is pulled out from the connection well 465, the operator may grasp the mating piece surface 481 and tilt the catheter assembly 400 such that one of the mating connectors 482 is situated in front of the mating collar surface 461. Then, the operator may tilt the catheter assembly in the opposite direction thereby freeing the mating piece 480 from the mating collar 460. Finally, the operator may separate the catheter assembly 400 from the mating collar 460 by pulling the assembly out of the receiving aperture 462.

The parameters for the other component pieces not mentioned for this exemplary embodiment are consistent with the corresponding component pieces disclosed above in the exemplary embodiment shown in FIG. 1 (e.g., the diameter of distal end 440 is smaller than the diameter of receiving aperture 462, attachment site 431 can be made by various adhesive methods known to one having ordinary skill in the catheter art as long as a contamination free seal is maintained, etc.).

Figure 5A:
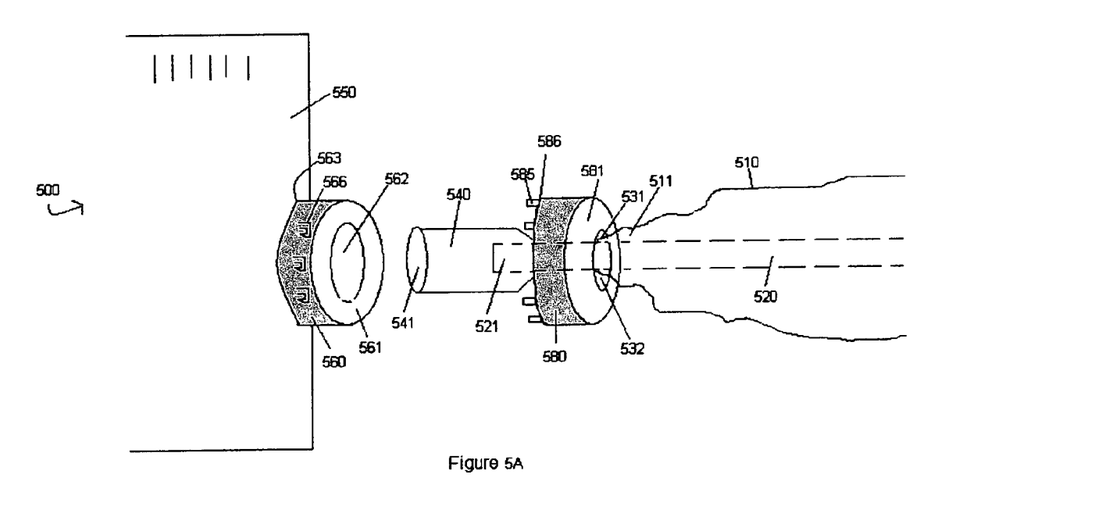
FIG. 5A shows a side view of a catheter assembly with mating projections at a distal portion of the catheter assembly according to an exemplary embodiment of the present invention.
Figure 5B:
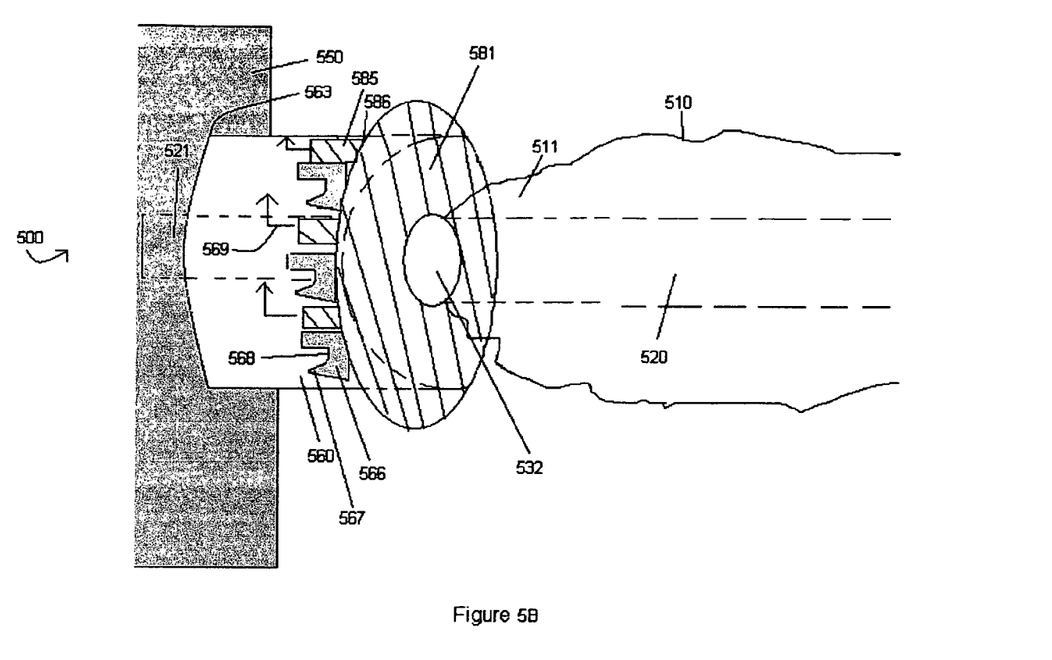
FIG. 5B shows a magnified side view of a catheter assembly with mating projections at a distal portion of the catheter assembly according to an exemplary embodiment of the present invention.

Another exemplary embodiment of the present invention incorporated into a catheter assembly 500 is shown in FIG. 5A and resembles, for example, a locking mechanism used to attach caps onto prescription drug containing bottles. The catheter assembly 500 includes a mating piece 580 situated at the distal end of the catheter assembly with mating projections 585, a catheter 520, a protective sheath 510, a distal end 540, a urine outlet 541, a collection receptacle 550, and a mating collar 560 with locking pieces 566. The mating projections 585 on the mating piece 580 can be composed of a conventional material commonly used in the catheter arts such that the mating projections 585 are rigid enough to avoid being broken off from their attachment points 586 on the mating piece 580 during the operator's manipulation of the catheter assembly 500. The mating projections 585 may be situated on the mating piece 580 in a uniform arrangement such that when the underside of the mating piece surface 581 makes contact with the mating collar surface 561, the mating 585 projections are dispersed among the locking pieces 566 as shown in FIG. 5B. Thus, the mating projections 585 on the mating piece 580 along with the locking pieces 566 on the mating collar 560 may both be uniformly spaced apart such that when the mating piece 580 is brought into contact with the mating collar 560 during connection, the mating projections 585 are situated adjacent to the locking pieces 566 as shown in FIG. 5B. The locking pieces 566 can be composed of a conventional material commonly used in the catheter arts such that the locking pieces are rigid enough to withstand an ordinary amount of friction and pressure. In particular, the tip 567 of the locking pieces 566 may be of such material and width that it does not break off during ordinary manipulation of catheter assembly 500.

During connection, the operator grasps the mating piece surface 581 with one hand and guides the mating piece 580 toward the mating collar surface 561 held by the other hand. Thus, the mating piece 580 and the receiving collar 560 may be in physical contact as shown in FIG. 5B. To complete the connection, the operator may push down on the mating piece surface 581 until the attachment point 586 is situated just below the tip 567 of the locking pieces 566. While maintaining the same downward force upon the mating collar surface 561, the operator then may rotate the mating piece 580 in a clockwise direction such that attachment point 586 is situated just below the tip 567 and in same horizontal plane as the cavity 568 of the locking pieces 566. This rotational clockwise movement is illustrated in FIG. 5B by the arrows 569. Then, the operator may release the grasp on the mating piece surface 581 thereby discontinuing the downward force upon the mating piece surface 581. The mating projections 585 therefore rebound and slide into the cavity 568 of the locking pieces 566. To disconnect the mating piece 580 from the receiving collar 560, the operator applies enough downward force such that the attachment point 586 of the mating projections 585 is situated just below the tip 567 and is far enough out of the cavity 568 to enable counter-clockwise rotation of the mating piece 580. The operator may rotate the mating piece 580 in a counter-clockwise direction while maintaining the downward force on the mating piece surface 581 such that the mating projections 585 are freed from the cavity 568 of the locking pieces 566. The operator may then release the mating piece surface 581 thereby allowing the mating piece 580 to rebound to rebound and resume its original position as depicted in FIG. 5B.

The cavity 568 may be of such a design such that it is able to receive the mating projections 585, and in the locked position it is able to securely maintain and prevent movement of the mating projections 585 and hence the mating piece 580 in the absence of the operator's force. The mating collar surface 581 may be of a diameter slightly larger than the diameter of the receiving collar 560 and mating piece 580 such that a gripping top (not shown) is formed thereby enabling the operator to better manipulate the catheter assembly 500. The diameter of the mating piece 580 may be of a diameter slightly larger than the diameter of the mating collar 560 such that the mating piece 580 is able to make contact with and extend over the mating collar surface 561 far enough to allow the operator to manipulate the mating projections 585 to connect and disconnect the mating piece 580 with the mating collar 560 as described above. The diameter of the mating piece 580 may be of such a diameter so as to provide a seal between the mating collar 560 and mating piece 580 when the mating projections 585 are situated inside the cavity 568 of the locking pieces 566.

Additionally, the inside of the mating piece 580 may contain an inner ring (not shown) made of a standard material commonly used in the catheter arts such that once connected to the mating collar surface 561, it provides a seal between the mating collar 560 and the mating piece 580. The inner ring may also be the source of the rebounding mechanism described above. In this embodiment, the inner ring may be of the same diameter as the mating collar 560 such that when in contact with the mating collar surface 561, the inner ring provides a seal between the mating collar 560 and the mating piece 580. The inner ring may be attached inside the mating piece 580 at its distal end just above the attachment site 586. The mating piece 580 may be of a diameter larger than the diameter of the mating collar 560 and ring such that it is able to be connected to the mating collar 560 and locked in place by pushing down on the mating piece surface 581 while rotating the mating piece 580 in a clockwise direction so as to allow the mating projections 585 to enter the cavity 568 of the locking pieces 566.

The parameters for the other component pieces not mentioned for this exemplary embodiment are consistent with the corresponding component pieces disclosed above in the exemplary embodiment shown in FIG. 1 (e.g., the diameter of distal end 540 is smaller than the diameter of receiving aperture 562, attachment site 531 can be made by various adhesive methods known to one having ordinary skill in the catheter art as long as a contamination free seal is maintained, etc.).

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A connecting device for a urinary catheter assembly, the device comprising:
   a hollow cylindrical body surrounding a distal portion of a urinary catheter assembly;
   a collar, having an inner diameter larger than the hollow circular body at a receiving end of a collection receptacle;

at least one pair of mating releases coupled with the body, each mating release having an outwardly extending short arm, a joining member located inside the body perpendicularly attached to the inner end of the short arm at a distal end of a joining member, and an outwardly extending long arm perpendicularly attached at an inner end with the proximal end of the joining member, and wherein the mating releases of each pair are located along opposite sides of the body;

wherein the body has an aperture for each arm protruding through the aperture; and a spring located in between each pair of mating releases and inside the body such that when a force pushes the mating releases towards each other, the spring pushes the mating releases away from each other;

wherein the mating releases are pushed together until the short arm no longer protrudes through the body and is flush with the body during insertion of the body into the collar;

wherein the body is inserted into the collar until the short arm passes an inside edge of the collar at which point the force applied to the mating release is released allowing the spring to force the mating release back into resting position where the collar locks between the short arm and the long arm of each mating release;

wherein the body mates with the collar thereby allowing fluid communication within the catheter assembly while maintaining a temporary or permanent seal preventing fluid communication with an external environment.

2. The device of claim 1, wherein the spring is composed of a metallic or plastic material.

3. A connecting device for a catheter assembly, the device comprising:

a circular body situated at a distal portion of a catheter assembly on or proximal to a urine outlet;

a collar, having an inner diameter larger than the hollow circular body, situated at a proximal portion of a collection receptacle, at least one pair of mating releases coupled with the body, each mating release having an outwardly extending short arm, a joining member located inside the body perpendicularly attached to the inner end of the short arm at a distal end of a joining member, and an outwardly extending long arm perpendicularly attached at an inner end with the proximal end of the joining member, and wherein the mating releases of each pair are located along opposite sides of the body;

wherein the body has an aperture for each arm protruding through the aperture; and a spring located in between each pair of mating releases and inside the body such that when a force pushes the mating releases towards each other, the spring pushes the mating releases away from each other;

wherein the mating releases are pushed inward until the short arm no longer protrudes through the body and is flush with the body during insertion of the body into the collar;

wherein the body is inserted into the collar until the short arm passes an inside edge of the collar at which point the force applied to the mating release is released allowing the spring to force the mating release back into resting position where the collar is suspended relative to the body between the short arm and the long arm of each mating release;

wherein the circular body mates with the collar thereby allowing fluid communication between the urine outlet and the collection receptacle while maintaining a temporary or permanent seal preventing fluid communication with an external environment.

4. The device of claim 3, wherein to separate the urinary catheter assembly from the collection receptacle, the mating releases are pushed inward until the short arms are flush with the body, then the body slides out from the collar, and the mating releases can be released to resting position.

* * * * *